(12) United States Patent
Zhong et al.

(10) Patent No.: US 9,994,533 B2
(45) Date of Patent: Jun. 12, 2018

(54) METHOD OF PREPARING ATG'S ANALOGUE, AND THE APPLICATION OF ATG AND IT'S ANALOGUE

(71) Applicant: Longhua Hospital Shanghai University of Traditional Chinese Medicine, Shanghai (CN)

(72) Inventors: Yifei Zhong, Shanghai (CN); Honggang Gu, Shanghai (CN)

(73) Assignee: Longhua Hospital Shanghai University of Traditional Chinese Medicine, Shanghai (CN)

( * ) Notice: Subject to any disclaimer, the term of this patent is extended or adjusted under 35 U.S.C. 154(b) by 0 days. days.

(21) Appl. No.: 15/461,494

(22) Filed: Mar. 17, 2017

(65) Prior Publication Data
US 2017/0313667 A1    Nov. 2, 2017

(30) Foreign Application Priority Data

Apr. 28, 2016  (CN) .......................... 2016 1 0278529
May 13, 2016  (CN) .......................... 2016 1 0320986
Dec. 12, 2016  (CN) .......................... 2016 1 1141821

(51) Int. Cl.
*C07D 271/06*    (2006.01)
(52) U.S. Cl.
CPC ................. *C07D 271/06* (2013.01)

(58) Field of Classification Search
CPC ................................................... C07D 271/06
See application file for complete search history.

(56) References Cited

PUBLICATIONS

Das et al, Tetrahedron Letters (2012), 53(31), 3947-3950.*

* cited by examiner

*Primary Examiner* — Sudhakar Katakam
(74) *Attorney, Agent, or Firm* — JCIPRNET (57) ABSTRACT

The present invention provides the use of ATG in the preparation of a reagent for adjusting the activity of PP2A; and the use of ATG in increasing the activity of PP2A in 293T cells. The present invention also provides the use of the arctigenin in the preparation of the medicine for reducing the proteinuria of the diabetic mice. The present invention also provides the use of the arctigenin in the preparation of the reagent for inhibiting the expression of the NOX4 gene. The present invention also provides analogs of arctigenin and application thereof. The present invention provides a novel use of ATG for modulating PP2A activity, and ATG can also significantly reduce proteinuria in diabetic mice. At the same time, arctigenin could significantly inhibit the expression of NOX4 in STZ-eNOS$^{-/-}$ mice glomeruli. The ATG analogs of the present invention are more effective than the native ATG.

4 Claims, 6 Drawing Sheets

METHOD OF PREPARING ATG'S ANALOGUE, AND THE APPLICATION OF ATG AND IT'S ANALOGUE

CROSS-REFERENCE TO RELATED APPLICATION

This application claims the priority benefit of China Application serial No. 2016102785299, filed on Apr. 28, 2016, the priority benefit of China Application serial No. 201610320986X, filed on May 13, 2016, and the priority benefit of China Application serial No. 2016111418212, filed on Dec. 12, 2016. The entirety of each of the above-mentioned patent applications is hereby incorporated by reference herein and made a part of this specification.

FIELD OF THE DISCLOSURE

The invention relates to the preparation method of ATG's analogue, and the application of ATG and it's analogue, and belongs to the field of Chinese traditional medicine.

BACKGROUND OF THE DISCLOSURE

Arctigenin (ATG) is the main monomer compounds in a Chinese traditional medicine named fructus arctii. Fructus arctii is widely used in the treatment of diabetes in clinical, but its mechanism of action and the effective composition is not clear. In this disclosure, the study found that the ATG significantly reduce proteinuria in diabetic mice.

PP2A is a serine threonine phosphorylase that regulates most of the phosphorylases in eukaryotic cells. In the signal transduction cascade, PP2A interacts with other phosphorylase and kinase, constitute macromolecule for the regulation of downstream signal transduction. In diabetic kidney disease (DKD) P65 is the key pathway leading to inflammation. PP2A can dephosphorylate P65 and thereby plays the role of treating the DKD. In addition, there are studies revealing that PP2A and proto-oncogene c-Myc are closely linked. The PP2A's regulatory subunit B56α selectively binds to the N-terminus of c-Myc, resulting in a significant reduction in c-Myc expression levels. Using shRNA to release the binding of B56α to c-Myc can lead to the overexpression of c-Myc, thus increasing the c-Myc Ser62's phosphorylation level and the enhancement of c-Myc's function and other similar phenomena. According to this, it is easy to conjecture that PP2A plays a key role in the regulation of cell proliferation and differentiation.

The clinical manifestations of diabetic nephropathy were persistent increasing of proteinuria and decreasing of glomerular filtration rate. The 24-hour total proteinuria of normal adult is less than 150 mg, and adolescents can be slightly higher but not more than 300 mg/24 h. When the total protein in the urine exceeded 300 mg/24 h was detected, that is known as proteinuria. Proteinuria is the most serious problem in patients with diabetic nephropathy, urinary protein content is not only related to the degree of renal damage, but also one of the main indicators of determining the progress of diabetic patients with chronic kidney disease. Urine of normal human contains very small amounts of protein, their urine protein is negative in routine examination. However, if the glomerular structure changes caused by renal disease, resulting in increasing glomerular filtration membrane permeability, it would make the protein in glomerular filtrate increased and beyond the renal tubular reabsorption capacity, thereby appears the proteinuria, in which the protein is mainly albumin. 24 hour urine albumin between 30-300 mg/24 h is referred as microalbuminuria which is an indicator of early diabetic nephropathy. Lowering proteinuria may reduce its continued damage to the kidneys.

Arctigenin (ATG) has a variety of biological activities. However, as a potential drug, even if it has a significant effect, in order to carry out a wide range of applications, as well as to improve the practical effect on the human body, it still needs further improvement. Natural ATG has the characteristics of low water solubility and easy decomposition in primary metabolites, which limits its further application. Therefore, how to improve the effect of the natural product ATG has become an urgent problem to be solved in the art.

SUMMARY OF THE DISCLOSURE

The invention relates to the application of ATG in a drug for regulating the bioactivity of PP2A, NOX4, and reducing the diabetic proteinuria.

The invention also relates to an ATG analogue which consists of three parts A, B and C, and the specific structure is shown as the following three general formulas:

15

14

16 wherein each of X/Y/Z is independently selected from the group consisting of C, N, S, O. $R_1$, $R_2$, $R_3$, $R_4$ and $R_5$ are each independently selected from H, $CH_3$, aliphatic or aromatic hydrocarbon groups, nitro groups, phosphoric acid groups, sulfide groups, sulfone groups, nitrile groups, heterocyclic group, boronate or boronic acid group, ester group, and amine group.

The invention also relates to a method for preparing the ATG analogue, characterized by comprising the steps of:

Step 1: The compound is first synthesized which is called compound C and synthetic of compound C is as follows:

Step 2: BT280 is then synthesized by boron reaction. The reaction formula is as follows:

Step 3:
BT282 was synthesized from BT280 and water-soluble 3MKHF$_2$. The reaction was as follows:

Step 4: BT282 is further acidified in the presence of silica and water to produce BT281. The reaction is as follows:

DETAILED DESCRIPTION

Hereinafter, embodiments of the present invention will be described with reference to the drawings.

Example 1

Figure 1:
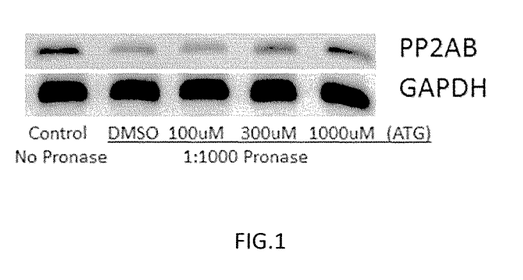
FIG. 1 is the result of the DARTS-western hybridization.

1. Mass Spectrometry Analysis after 293T Stimulated by ATG 293T cells were digested with M-PER mammalian protein extraction buffer (78501 ThermoFisher) and phosphatase inhibitor (50 mM NaF, 10 mM β-glycerophosphate, 5 mM sodium pyrophosphate, 2 mM Na3VO4); and the protein concentration is determined by Bradford method (500-0006 Bio-rad). ATG was either added or not in the cell lysate. If added, the concentration of ATG was 300 μM. The cells were incubated at room temperature for 1 h. The cells were then lysed by incubating for 20 minutes at room temperature with different concentrations of pronase at 1:1000 (10165921001, Roche). The two groups of lysates are subjected to mass spectrometry and then compared. The results are shown in Table 1.

was formulated at 3 different concentrations: 100 μM, 300 μM, 1000 μM. So there are 5 groups of Western Blot: blank group (without addition of pronase), DMSO (pronase 1:1000), ATG 100 μM (pronase 1:1000), ATG 300 μM (pronase 1:1000), ATG 1000 μM (Pronase 1:1000). As a result, it was found that PP2A binding increased with the increasing concentration of ATG under the condition of pronase 1:1000, and the results are shown in FIG. 1. While pronase can digest proteins, it digests more ATG-unbinding proteins than ATG-binding proteins. We tested different concentrations of pronase and found that a concentration of 1:1000 can help us to identify ATG-binding and ATG-unbinding proteins better, which are used to study the binding proteins of small molecules. This method is called DARTS.

In FIG. 1: DARTS-western blot confirmed the binding of ATG to PP2AB; PP2A had three structural units, and ATG bound to the catalytic unit. The catalyst unit of the protein called PP2AB, the gene called PPP2CB.

If need to extract PP2A protein, then do not add pronase, and use the following steps:

Step 1: Add 100 μM to 1000 μM ATG to stimulate the cells.

Step 2: Extracting the cells and crushing;

TABLE 1

Comparison results of mass spectrometry after ATG intervention

| Identification of proteins (3004) | Search name | Molecular weight | Spectral Count (ATG) | Spectral Count (DMSO) | Ratio (ATG/DMSO) |
|---|---|---|---|---|---|
| Tubulin beta-3 chain OS = Homo sapiens GN = TUBB3 PE = 1 SV = 2 | TBB3_HUMAN | 50 kDa | 49 | 0 | 25.6 |
| Tubulin beta-6 chain OS = Homo sapiens GN = TUBB6 PE = 1 SV = 1 | TBB6_HUMAN | 50 kDa | 25 | 0 | 13.6 |
| Serine/threonine-protein phosphatase 2A catalytic subunit beta isoform OS = Homo sapiens GN = PPP2CB PE = 1 SV = 1 | PP2AB_HUMAN | 36 kDa | 14 | 0 | 7.8 |
| Heterogeneous nuclear ribonucleoprotein H2 OS = Homo sapiens GN = HNRNPH2 PE = 1 SV = 1 | HNRH2_HUMAN | 49 kDa | 12 | 0 | 6.8 |
| Keratin, type II cytoskeletal 6A OS = Homo sapiens GN = KRT6A PE = 1 SV = 3 | K2C6A_HUMAN (+1) | 60 kDa | 8 | 0 | 5.2 |
| Keratin, type I cytoskeletal 17 OS = Homo sapiens GN = KRT17 PE = 1 SV = 2 | K1C17_HUMAN | 48 kDa | 7 | 0 | 4.7 |
| Protein transport protein Sec61 subunit alpha isoform 1 OS = Homo sapiens GN = SEC61A1 PE = 1 SV = 2 | S61A1_HUMAN | 52 kDa | 7 | 0 | 4.7 |
| Keratin, type II cytoskeletal 5 OS = Homo sapiens GN = KRT5 PE = 1 SV = 3 | K2C5_HUMAN | 62 kDa | 7 | 0 | 4.7 |

Analysis of the mass spectrometry results shows that the two proteins which have the largest binding amount are belonged to tubulin, which is considered nonspecific due to the high intracellular tubulin content. Furthermore, since the content of PP2A in cells is very low in the normal state, it is considered that the binding ratio of ATG and PP2A is high.

2. The Binding of ATG and PP2A was Detected by Western Blot.

We used ATG to stimulate 293T cells. After selecting the optimum concentration of pronase, we chose different concentrations of ATG to stimulate 293T cells to observe whether the binding amount of ATG and PP2A increased with the increase of ATG concentration. The applied ATG Step 3: Loading and carrying out polyacrylamide gel electrophoresis;

Step 4: Cut the gel band corresponding to the molecular weight of PP2A and recover the protein. When recovering the protein, the gel strips were crushed with a grinding rod, and a buffer of less than 500 μl per block of gel was added, left to stand at 4° C. for 10 hours, and then centrifuged at 5000-10000 rpm for 10 min. The supernatant contains PP2A protein. The recovery of protein by this method was 70%.

The cells in step one could be 293T cells, or could be other types of cells.

3. Effect of ATG on PP2A Activity

Figure 2:
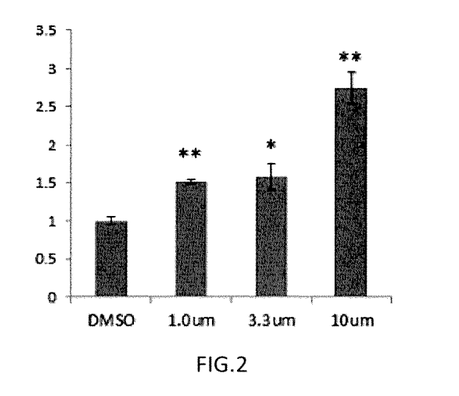
FIG. 2 is the activity of PP2A alter stimulation with different concentrations of ATG.

Immortal podocytes were stimulated with ATG at concentrations of 0, 1.0 μm, 3.3 μm, and 10 μm, and the stimulation time was 1 hour. The activity of PP2A was detected by PP2A activity kit (R & D systems, DYC3309-2). It was found that the activity of PP2A is increased with the increase of ATG concentration. The results are shown in Table 2 and FIG. 2. The results show that ATG could effectively increase the activity of PP2A. With the increase of the amount of ATG, the activity of PP2A also increased.

TABLE 2

PP2A activity values

|  | DMSO | 1.0 μm | 3.3 μm | 10 μm |
|---|---|---|---|---|
| Mean ± standard deviation | 0.0176 ± 0.0009 | 0.0268 ± 0.0004 | 0.0279 ± 0.0030 | 0.0484 ± 0.0036 |
| P values |  | 0.006 | 0.044 | 0.007 |

Note:
P values are compared with DMSO.

Example 2

The detection method of Western Blot and mRNA used in the present embodiment is a detection method commonly used by person skilled in the art, and the specific detection method is described in "Molecular Biology Laboratory Manual" (People's Military Medical Press, published in 2011 Jun. 1).

1. Arctigenin (ATG) can significantly reduce proteinuria in diabetic kidney disease mice.

Figure 3:
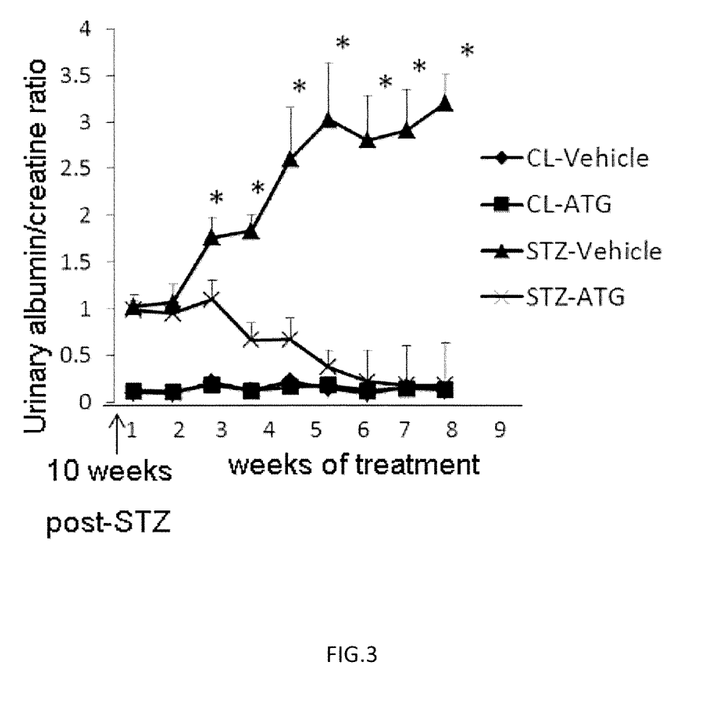
FIG. 3 is a graph showing the experimental results of administrating arctigenin to diabetic mouse model.
Figure 4:
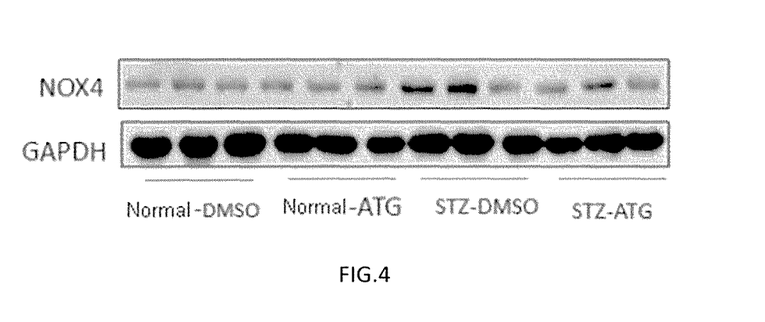
FIG. 4 is a graph showing the protein expression of arctigenin administered STZ-eNOS$^{-/-}$ mouse glomerulus NOX4.

When the mice were 6 weeks of age, streptozotocin (STZ)-induced diabetic nephropathy models were started by tail vein injection. The specific method is: STZ in accordance with the amount of 50 mg/kg is injected in tail vein. 72 hours after the injection, determine whether the modeling is successful by determining the level of blood glucose and urine. When the blood glucose level is more than 16 mmol/L and urine glucose level is between +++ and ++++, the model was considered successful. After 10 weeks of STZ injection, ATG was orally administered at a dose of 40 mg/kg once daily. The control group was given the same volume of DMSO (dimethyl sulfoxide) orally. Treatment was for 8 weeks. Urine protein levels were measured in each group. The number of the mice in each group is 10 in Table 3. Results as shown in Table 3 and FIG. 3 demonstrate that ATG significantly reduces proteinuria, and the effect is superior to the ACEI/ARBs that is widely used currently. ACEI: angiotensin converting enzyme inhibitors; ARBs: angiotensin receptor blockers.

TABLE 3

Experimental results of ATG reduced proteinuria

|  | 0 week | 1 week | 2 week | 3 week | 4 week | 5 week | 6 week | 7 week | 8 week |
|---|---|---|---|---|---|---|---|---|---|
| Normal group | 0.10 ± 0.02 | 0.09 ± 0.02 | 0.21 ± 0.02 | 0.12 ± 0.03 | 0.22 ± 0.04 | 0.14 ± 0.03 | 0.09 ± 0.03 | 0.16 ± 0.04 | 0.12 ± 0.03 |
| Normal group - ATG | 0.12 ± 0.03 | 0.11 ± 0.05 | 0.18 ± 0.04 | 0.12 ± 0.03 | 0.16 ± 0.04 | 0.18 ± 0.02 | 0.12 ± 0.06 | 0.14 ± 0.05 | 0.13 ± 0.04 |
| Model group | 1.02 ± 0.14 | 1.06 ± 0.20 | 1.76 ± 0.22 | 1.83 ± 0.18 | 2.6 ± 0.56 | 3.02 ± 0.62 | 2.80 ± 0.48 | 2.91 ± 0.44 | 3.20 ± 0.32 |
| ATG Model group - ATG | 0.98 ± 0.11 | 0.95 ± 0.12 | 1.10 ± 0.21 | 0.66 ± 0.19 | 0.66 ± 0.23 | 0.37 ± 0.18 | 0.22 ± 0.34 | 0.18 ± 0.42 | 0.18 ± 0.45 |

Oxidative stress is considered to be a key pathogenic factor in the emergence and development of diabetic nephropathy. Many studies have confirmed that both in the laboratory model of diabetic nephropathy or in the body of diabetes patients there are oxidative stress phenomenon. Oxidative stress, refers to when the body subjected to various harmful stimuli, the free radicals and their active derivatives increased, and at the same time, the ability of antioxidant systems decreased, the degree of oxidation thereby exceeds the removal of oxides, causing imbalance between the oxidation system and antioxidant system and leading to tissue damage. There are many enzyme systems in the kidney that produce ROS, such as the nicotinamide adenine dinucleotide phosphate oxidase (NADPH oxidase, NOX) system. The kidney is one of the organs sensitive to oxidative processes. The present invention proves that arctigenin has remarkable inhibiting effect on the expression of NOX4, and reveals that arctigenin regulates the expression of NOX4, thereby alleviating the symptoms of proteinuria in diabetic nephropathy patients.

2. ATG can decrease NOX4's protein and mRNA expression in glomeruli of STZ-eNOS$^{-/-}$ mice.

The results of Western Blot demonstrated that the NOX4's protein expression in glomerular of STZ-eNOS' mice administered with ATG was significantly less than that of the untreated group.

TABLE 4

Statistical results of Western Blot data

| NOX4/GAPDH | mean | standard deviation |
|---|---|---|
| Normal group-DMSO | 0.13 | 0.03 |
| Normal group-ATG | 0.13 | 0.02 |
| STZ-DMSO | 0.27 | 0.05 |
| STZ-ATG | 0.14 | 0.04 |

Figure 5:
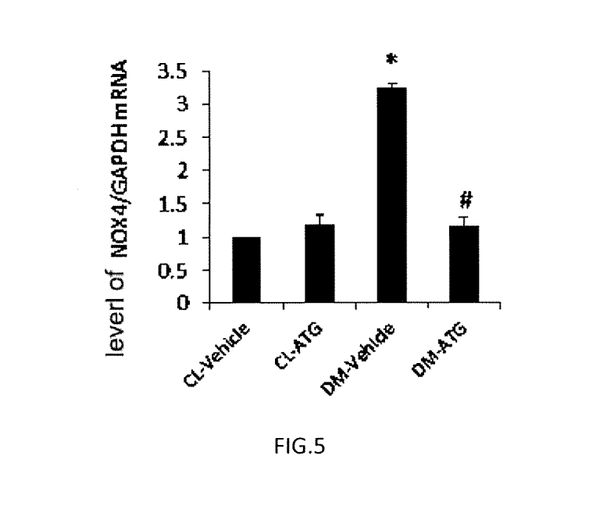
FIG. 5 is the result of mRNA expression of the arctigenin administered STZ-eNOS' mouse glomerular NOX4 gene.

Further, the mRNA of the glomeruli was extracted and subjected to RT-PCR. The results show that ATG significantly reduced mRNA expression of NOX4 gene. The results are shown in FIG. 5.

3. ATG can reduce protein and mRNA expression of NOX4 in human immortal podocytes and endothelial cells.

Figure 6:
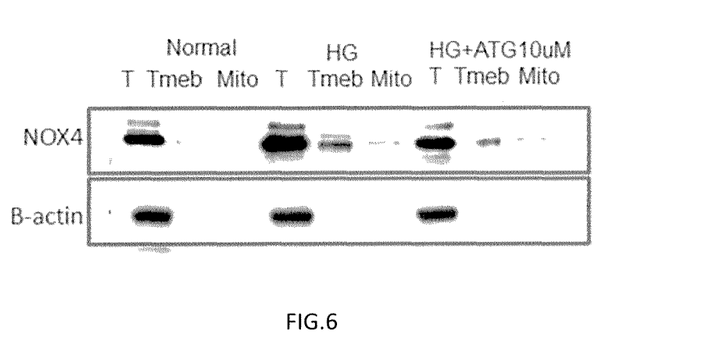
FIG. 6 is a graph of the NOX4 protein expression in human immortal podocytes.
Figure 7:
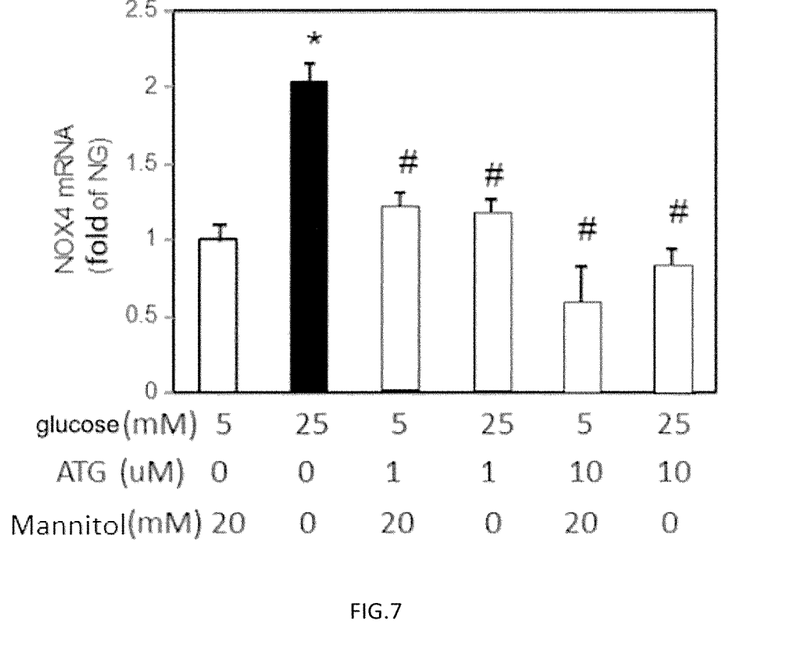
FIG. 7 is a graph of an mRNA expression of the NOX4 gene in human immortal podocytes administered by ATG.

3.1 Western blot and Realtime PCR confirmed that ATG in human immortal podocytes can inhibit the overexpression of NOX4 caused by high glucose stimuli, see table 5 and FIG. 6. The expression of NOX4 in the total protein, membrane protein and mitochondrial protein of human immortal podocytes was detected in the experiment. The results show that the expression of NOX4 in total protein, membrane protein and mitochondrial protein increases under high glucose environment, while ATG can inhibit the expression of NOX4 in the above three kinds of structures. The amount of ATG added to human immortal podocytes was 10 μmol/L. FIG. 7 shows that ATG is able to inhibit the overexpression of NOX4 mRNA in human immortal podocytes induced by high glucose.

The meanings of the symbols in FIG. 6 are as follows: HG: high glucose (glucose 25 mM); T: total protein; Tmeb cell membrane protein; Mito: mitochondrial protein.

TABLE 5

Statistical results of Western blot of NOX4 protein in podocytes

| T-NOX4/β-actin | mean | standard deviation |
|---|---|---|
| Normal group-DMSO | 1.17 | 0.25 |
| High glucose-DMSO | 2.57 | 0.15 |
| High glucose-ATG | 1.13 | 0.35 |

Figure 8:
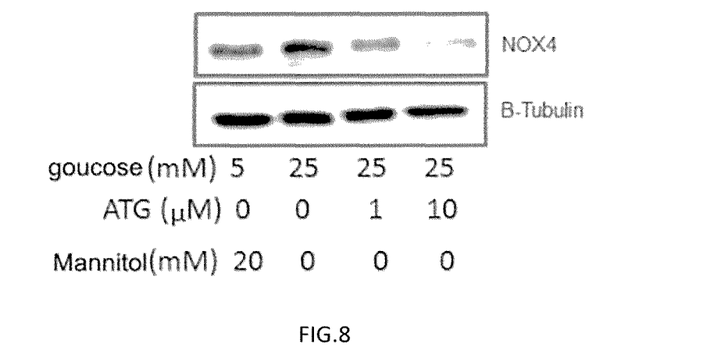
FIG. 8 is a graph showing the NOX4 protein expression of endothelial cells administered by ATG.

3.2 Western blot and Realtime PCR confirmed that ATG could inhibit the overexpression of NOX4 in mouse's primary endothelial cells. The dose of ATG for stimulating endothelium is shown in FIG. 8. The dose of 1 and 10 μmol/L corresponds to the last two bands. As shown in Table 6, ATG inhibited the overexpression of NOX4 protein in mouse primary endothelial cells induced by high glucose.

TABLE 6

Statistical results of Western blot of NOX4 protein in endothelial cells

| NOX4/B-Tubulin | Mean | standard deviation |
|---|---|---|
| Normal group | 0.21 | 0.03 |
| High glucose + DMSO | 0.80 | 0.15 |
| High glucose ATG 1 uM | 0.18 | 0.03 |
| High glucose ATG 10 uM | 0.12 | 0.03 |

Figure 9:
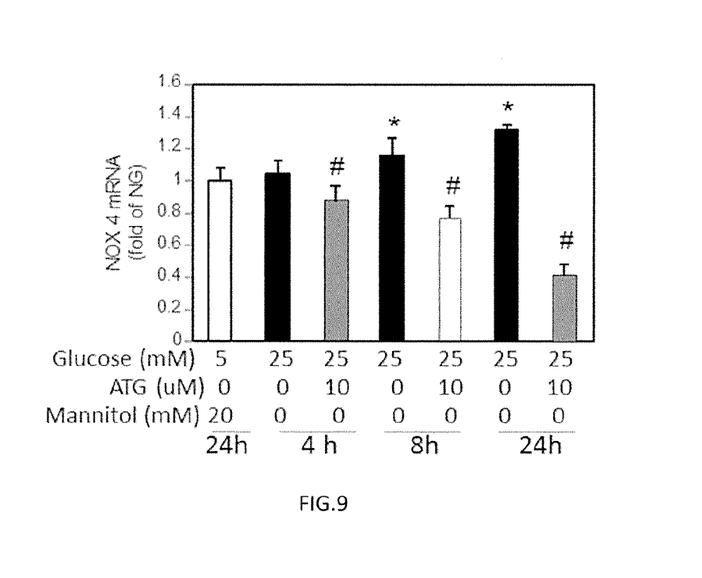
FIG. 9 is a graph showing the mRNA expression of NOX4 gene of endothelial cells administered by ATG.

As shown in FIG. 9, ATG inhibited the overexpression of NOX4 mRNA induced by high glucose in mouse primary endothelial cells.

4. ATG can inhibit NOX from producing reactive oxygen species ROS

The human immortal podocytes were divided into 6 groups: blank group, high glucose group (30 mM), high glucose+10 μMATG, high glucose+20 μMATG, high glucose+50 μMATG, high glucose+100 μMATG.

Figure 10:
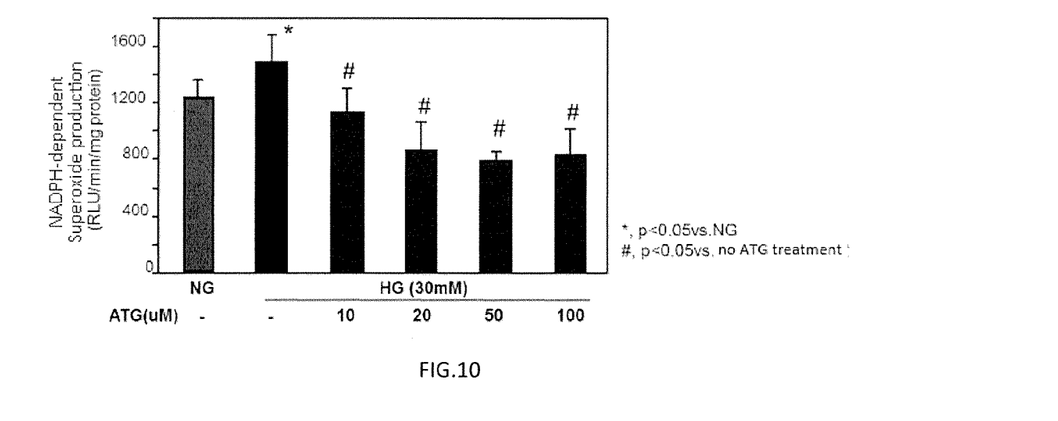
FIG. 10 is showing the effect of ATG on NOX-related ROS induced by high glucose.

The effects of ATG on NOX producing ROS were observed by measuring the oxidative activity of NADPH (reduced coenzyme II): The mouse endothelial cells were washed twice with HBSS (Hanks balanced salt solution), during which the cell culture dish was placed on ice. The cells were scraped with frozen HBSS containing protease inhibitors, then homogenated. The protein concentration was measured and calculated. 30 μg protein was added to each well and 25 μM glaucoma (Santa Cruz) and 200 μM NADPH (Cayman Chemical) were also added. After staying in the dark room for 10 minutes at 37° C., the luminescence of each well was measured. Results: There was significant difference of ROS between high glucose group and normal group (P<0.05). The different concentration of ATG (10 μM, 20 μM, 50 μM, 100 μM) could reduce the amount of ROS induced by NOX. See Table 7 and FIG. 10 for the details.

TABLE 7

Effects of ATG on NOX-related ROS induced by high glucose

| | NG | HG | HG + 10 μM | HG + 20 μM | HG + 50 μM | HG + 100 μM |
|---|---|---|---|---|---|---|
| Mean ± standard deviation | 1238 ± 128 | 1480 ± 210 | 1030 ± 164 | 864 ± 191 | 794 ± 51 | 832 ± 176 |

Example 3

The present invention provides a series of ATG analogues as follows: It consists of three parts, A, B and C, and part B has open-loop and closed-loop forms. In both cases, X, Y, Z are selected from C, N, S and O, respectively. $R_1$, $R_2$, $R_3$, $R_4$ and $R_5$ are each independently selected from H, $CH_3$, aliphatic or aromatic hydrocarbon groups, nitro groups, phosphoric acid groups, sulfide groups, sulfone groups, nitrile groups, heterocyclic group, boric acid ester or boronic acid group, an ester group, and an amine group.

Further, the above-mentioned analogues also include compounds with part B as an open-ring structure as follows:

By Introducing boron-containing pharmacophore in ATG, the lactone ring would change to oxadiazole ring, so that it has more hydrophilic characteristics and increases water solubility as much as possible. After screening, three compounds named BT280, BT281 and BT282 have the best effect.

Arctigenin (ATG)

BT282

Arctigenin (ATG)

BT280

BT281

BT282

(1) The structural features of ATG analogues:

The boron-containing pharmacophore, the boron-containing group, can not only bind to the target protein by hydrogen bonding, but also produce bioactivity by bonding through covalently bond. Therefore, three compounds, BT280, BT281, and BT282, were identified by ATG as the target. Specific structures are shown in the above chemical formulas.

The synthetic ATG homolog structure is shown in the above chemical formula. The original ATG consists of three parts, part A is the phenyl ring derivative, part B is the lactone ring and part C is the phenyl ring system. In part B, the lactone ring was modified to be an oxadiazole ring, giving it more hydrophilic character to increase water solubility as much as possible. In Part C, by introducing boronic acid ester instead of phenyl ring, boron-containing groups could bond with the target protein not only by hydrogen bond but also by covalently bond to produce biological activity. In Part A, replacing the phenyl ring derivative with trimethoxy to increase the hydrophobic character of the cross-cell membrane and protect the hydroxyl group from terminating in primary metabolism. Three compounds, BT280, BT281 and BT282, were synthesized.

Figure 11:
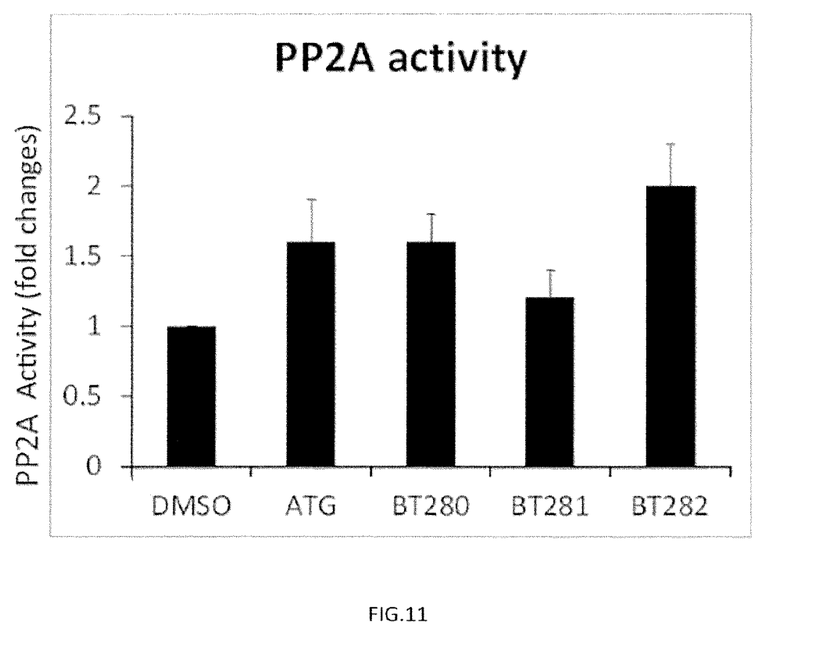
FIG. 11 is the effect of the ATG analogues in present invention on PP2A activity.

(2) Biological activity of ATG analogues:

The biological activities of the three compounds were determined by measuring the downstream PP2A activity and the degree of phosphorylation of NF-kB. The results are shown in FIG. 11, DMSO was used as a reference. 293T cells were stimulated respectively with native ATG and new compounds BT280, BT281, BT282. The concentrations of ATG and the three new compounds were 10 μM. The results show that the effect of BT280 on PP2A activity was similar to that of native ATG. The effect of BT281 on PP2A activity was weaker than that of native ATG, but still stronger than DMSO group. Compound BT282 had higher activity to PP2A than natural ATG. Therefore, all three compounds can be used to improve the biological activity of PP2A.

Figure 12:
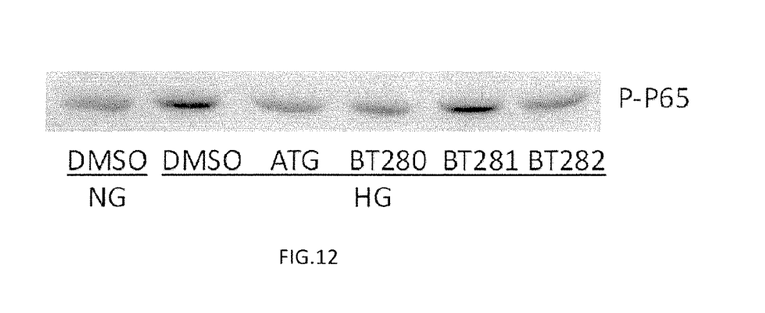
FIG. 12 is the effect of the ATG analogues in present invention on the degree of NF-kB phosphorylation.

Obviously, BT282 is the best choice to improve the activity of PP2A. BT280 and BT281 did not show a significant ability to increase the activity of PP2A compared to natural ATG. However, BT280 and BT281 have better water-solubility and better bioreactive groups than native ATG, suggesting that they can provide better drug delivery in animal-level treatment. For example, because of its better water solubility, it can be better through the animal's circulatory system to reach the affected area, and to achieve higher concentrations, so as to achieve better drug delivery effect. The results of the phosphorylation of NF-KB are shown in FIG. 12. The degree of phosphorylation of NF-κB was found to correspond to that of PP2A in FIG. 11, suggesting that the role of ATG analogues in the NF-kB pathway is similar to ATG, which Indicates that ATG analogues can also be used to modulate the phosphorylation of NF-kB. In the results of FIG. 12, the stimulation concentration of ATG analogues was 10 μM.

In summary, BT282 is the best target compound. BT282 has a much better effect than ATG. However, the other two compounds are also useful. BT280 and BT281 could be used as potential drug targets in specific biological experiments because they are more advantageous in water solubility than natural ATG, although BT280 and BT281 have no advantage in activating PP2A compared with natural ATG.

The synthesis of ATG analogues is shown in the following examples

Example 4

First, the following compounds were synthesized:

hereinafter referred to as compound C. Then BT280 was synthesized by boron-based reaction, BT282 (trifluoro potassium salt) was synthesized from BT280 and water soluble 3MKHF$_2$. The trifluoro potassium salt complex is then further acidified under the conditions of silica and water to get the BT281 boronic acid derivative.

Synthesis of Compound C:

In the above chemical reaction formula, compound A was trimethoxybenzoic acid in an amount of 0.9 mmol; compound B was used in an amount of 1.1 mmol in the presence of catalytic CDI (N, N'-dicyclohexylcarbodiimide) which was dissolved in 1.8 ml of DMF, then stirred at room temperature for 30 minutes to synthesize XB-A-26 (C). XB-A-26 was added in an amount of 1.4 mmol, and the reaction mixture was heated under reflux at 75° C. for 36 hours, monitored by TLC. The mixture was poured into 20 mL of water and extracted with EtOAc (3×10 mL). The combined layers were dried by Na$_2$SO$_4$, filtered and concentrated in vacuo. The crude product was purified by silica gel (hexane:EtOAc=3:1) to get the oxadiazole product as a white solid, which can collect 0.25 g of the final product C.

Synthesis of BT280:

BT280 Synthesis Steps:

Compound C (0.75 mmol), B2Pin2 (1.05 mmol), ACOK (3.80 mmol), Pd (PPh3)$_2$Cl$_2$ (0.075 mmol), and DMSO (15 mL) were charged into a 50 mL round bottom flask. The mixture was stirred at room temperature for 10 minutes, and the resulting mixture was stirred at 85° C. for 1 day. The mixture was diluted with water (30 ml) and extracted with ethyl acetate (3×30 ml). The organic layer was dried by sodium sulfate and concentrated in vacuo. The resulting product was subjected to a purification column extraction, and obtained 0.05 g of pure BT280.

BT282:Potassium trifluoro (4-(5-(3,4,5-trimethoxy-phenyl)-1,2,4-oxadiazol-3-yl) phenyl) borate Synthesis Steps:

BT280 (0.28 mmol) was added to 15 mL of MeOH, then 3M of KHF$_2$ was added, and after stirring for 2 hours, MeOH was evaporated to get a residue. The residue was dissolved in acetone and filtered, and the filtrate was evaporated to dryness to get a white solid, which was further eluted with EtOAC to get pure product. Ultimately, the weight of the pure product is 62 mg.

Synthesis of BT281: (4-(5-(3,4,5-trimethoxyphenyl)-1,2,4-oxadiazol-3-yl) phenyl)

Procedure: BT282 (36 mg) and silica gel (0.18 mmol) were added to H2O/ethyl acetate (1.0 mL). The reaction mixture was stirred at room temperature until the reaction was complete. The reaction mixture was filtered to remove the silica gel and the filter cake was washed with acetone. The organic phase was separated and the organic layer was dried to get the desired product BT281.

Example 5

First, the following compounds were synthesized:

hereinafter referred to as compound C. BT280 was then synthesized by boron-based reaction, and BT282 (trifluoro potassium salt) was synthesized from BT280 and water soluble 3MKHF₂. The trifluoro potassium salt complex is then further acidified under the conditions of silica and water to get the BT281 boronic acid derivative.

Synthesis of Compound C:

In the above chemical reaction formula, compound A was trimethoxybenzoic acid in an amount of 0.9 mmol; compound B was used in an amount of 1.1 mmol in the presence of catalytic CDI (N, N'-dicyclohexylcarbodiimide) which was dissolved in 1.8 ml of DMF, then stirred at room temperature for 30 minutes to synthesize XB-A-26 (C). XB-A-26 was added in an amount of 1.3 mmol, and the reaction mixture was heated under reflux at 80° C. for 24 hours, monitored by TLC. The mixture was poured into 20 mL of water and extracted with EtOAc (3×10 mL). The combined layers were dried by Na₂SO₄, filtered and concentrated in vacuo. The crude product was purified by silica gel (hexane:EtOAc=3:1) to get the oxadiazole product as a white solid, which can collect 0.3 g of the final product C.

BT280 Synthesis Steps:

Compound C (0.77 mmol, 0.30 g), B2Pin2 (1.07 mmol) ACOK (3.85 mmol, 0.377 g), Pd (PPh3)₂Cl₂ (0.077 mmol, 0.054 g), and DMSO (15 mL) were charged into a 50 mL round bottom flask. The mixture was stirred at room temperature for 10 minutes, and the resulting mixture was stirred at 85° C. for 1 day. The mixture was diluted with water (30 ml) and extracted with ethyl acetate (3×30 ml). The organic layer was dried by sodium sulfate and concentrated in vacuo. The resulting product was subjected to a purification column extraction, and obtained 0.06 g of pure BT280.

BT282:Potassium trifluoro (4-(5-(3,4,5-trimethoxyphenyl)-1,2,4-oxadiazol-3-yl) phenyl) borate Synthesis Steps:

BT280 (0.29 mmol, 0.12 g) was added to 15 mL of MeOH, then 3M of KHF₂ was added, and after stirring for 2 hours, MeOH was evaporated to get a residue. The residue was dissolved in acetone and filtered, and the filtrate was evaporated to dryness to get a white solid, which was further eluted with EtOAC to get pure product. Ultimately, the weight of the pure product is 65 mg.

Synthesis of BT281: (4-(5-(3,4,5-trimethoxyphenyl)-1,2,4-oxadiazol-3-yl) phenyl)

Procedure: BT282 (37 mg, 0.9 mmol) and silica gel (0.18 mmol, 11 mg) were added to H$_2$O/ethyl acetate (1.0 mL). The reaction mixture was stirred at room temperature until the reaction was complete. The reaction mixture was filtered to remove the silica gel and the filter cake was washed with acetone. The organic phase was separated and the organic layer was dried to get the desired product BT281.

Example 6

First, the following compounds were synthesized:

hereinafter referred to as compound C. BT280 was then synthesized by boron-based reaction, BT282 (trifluoro potassium salt) was synthesized from BT280 and water soluble 3MKHF$_2$. The trifluoro potassium salt complex is then further acidified under the conditions of silica and water to get the BT281 boronic acid derivative.

Synthesis of Compound C:

In the above chemical reaction formula, compound A was trimethoxybenzoic acid in an amount of 1.1 mmol; compound B was used in an amount of 1.3 mmol in the presence of catalytic CDI (N, N'-dicyclohexylcarbodiimide) which was dissolved in 1.8 ml of DMF, then stirred at room temperature for 30 minutes to synthesize XB-A-26 (C). XB-A-26 was added in an amount of 1.3 mmol, and the reaction mixture was heated under reflux at 75° C. for 20 hours, monitored by TLC. The mixture was poured into 20 mL of water and extracted with EtOAc (3×10 mL). The combined layers were dried by Na$_2$SO$_4$, filtered and concentrated in vacuo. The crude product was purified by silica gel (hexane:EtOAc=3:1) to get the oxadiazole product as a white solid, which can collect 0.31 g of the final product C.

BT280 Synthesis Steps:

Compound C (0.75 mmol), B2Pin2 (1.08 mmol) ACOK (3.88 mmol), Pd (PPh3) 2Cl$_2$ (0.079 mmol), and DMSO (15 mL) were charged into a 50 mL round bottom flask. The mixture was stirred at room temperature for 10 minutes, and the resulting mixture was stirred at 80° C. for 1 day. The mixture was diluted with water (30 ml) and extracted with ethyl acetate (3×30 ml). The organic layer was dried by sodium sulfate and concentrated in vacuo. The resulting product was subjected to a purification column extraction, and obtained 0.07 g of pure BT280.

BT280

BT281

BT282: Potassium trifluoro (4-(5-(3,4,5-trimethoxyphenyl)-1,2,4-oxadiazol-3-yl) phenyl) borate

Synthesis Steps:

BT280 (0.32 mmol) was added to 15 mL of MeOH, then 3M of $KHF_2$ was added, and after stirring for 2 hours, MeOH was evaporated to get a residue. The residue was dissolved in acetone and filtered, and the filtrate was evaporated to dryness to get a white solid, which was further eluted with EtOAC to get pure product. Ultimately, the weight of the pure product is 66 mg.

Synthesis of BT281: (4-(5-(3,4,5-trimethoxyphenyl)-1,2,4-oxadiazol-3-yl) phenyl)

Procedure: BT282 (39 mg) and silica gel (0.18 mmol, 11 mg) were added to $H_2O$/ethyl acetate (1.0 mL). The reaction mixture was stirred at room temperature until the reaction was complete. The reaction mixture was filtered to remove the silica gel and the filter cake was washed with acetone. The organic phase was separated and the organic layer was dried to get the desired product BT281.

What is claimed is:

1. An ATG analogue for regulating the bioactivity of PP2A, NOX4, and reducing diabetic proteinuria, wherein the ATG analogue is at least one compound selected from the group of compounds represented by formula (1-1) and formula (1-2):

formula (1-1)

formula (1-2)

wherein in formula (1-1) and formula (1-2):

X is O, Y is N, and Z is N;

$R_1$, $R_2$, $R_3$, $R_4$ and $R_5$ are each independently selected from H, aliphatic or aromatic hydrocarbon groups, nitro groups, phosphoric acid groups, sulfide groups, sulfone groups, nitrile groups, heterocyclic group, boronate or boronic acid group, ester group, and amine group.

2. The ATG analogue according to claim 1, wherein $R_2$ is $H_3CO$— and $R_3$ is $H_3CO$—.

3. The ATG analogue according to claim 1, wherein $R_4$ is $H_3CO$—.

4. The ATG analogue according to claim 1, wherein $R_2$ is $H_3CO$—, $R_3$ is $H_3CO$—, and $R_4$ is $H_3CO$—.

* * * * *